United States Patent [19]

Itoh

[11] 4,014,915
[45] Mar. 29, 1977

[54] OXIME CARBONATES
[75] Inventor: Masumi Itoh, Takatsuki, Japan
[73] Assignee: Fujisawa Pharmaceutical Co., Ltd., Osaka, Japan
[22] Filed: Aug. 26, 1975
[21] Appl. No.: 607,758
[30] Foreign Application Priority Data
Apr. 22, 1975 United Kingdom ............ 16707/75
[52] U.S. Cl. .................... 260/463; 260/112.5 R; 260/239.1; 260/308 B; 260/308 R
[51] Int. Cl.² ..................................... C07C 69/96
[58] Field of Search .................................. 260/463

[56] References Cited
UNITED STATES PATENTS

| | | |
|---|---|---|
| 3,095,408 | 6/1963 | Anderson et al. ............. 260/463 |
| 3,117,987 | 1/1964 | Horrom ......................... 260/463 |
| 3,219,694 | 11/1965 | Yates et al. ..................... 71/98 |
| 3,234,255 | 2/1966 | Hackmann et al. ............. 71/98 |
| 3,234,255 | 2/1966 | Hackmann et al. ............. 260/463 |
| 3,624,091 | 11/1971 | Daum et al. .................... 260/463 |
| 3,624,091 | 11/1971 | Daum et al. .................... 260/463 |
| 3,832,375 | 8/1974 | Itoh ................................. 260/463 |
| 3,895,046 | 7/1975 | Boroschewski et al. ........ 260/463 |
| 3,931,285 | 1/1976 | Morozowich ................... 260/463 |

FOREIGN PATENTS OR APPLICATIONS 1,226,739   3/1971   United Kingdom ............ 260/463

OTHER PUBLICATIONS

Beilstein: Handbuch der Organischen Chemie, vol. 10, pp. 660 & 662–664 (1927).
Bull. Chem. Soc. Jap. 38, No. 9, pp. 1525 (1965).
J.A.C.S. 79, (1957) pp. 6180–6183.
J. Chem. Soc. (1966) pp. 346–350.

Primary Examiner—Lewis Gotts
Assistant Examiner—D. R. Phillips
Attorney, Agent, or Firm—Bierman & Bierman

[57] ABSTRACT

Novel carbonic acid esters are disclosed which are useful in a process for introducing esterified carboxy-type protective groups on amino and/or imino groups in amino and/or imino group - containing compounds for the temporary protection of said amino and/or imino groups. Additionally, processes for preparing said esters are also disclosed.

24 Claims, No Drawings

OXIME CARBONATES

The present invention relates to a new carbonic acid ester which is useful as an agent for introducing esterified carboxy-type protective groups on amino and/or imino groups in amino and/or imino group-containing compounds and to processes for the preparation thereof.

Further, the present invention relates to a process for the temporary protection of amino and/or imino groups in amino and/or imino groups-containing compounds with esterified carboxy-type protective groups.

It is known that temporary protection of amino and/or imino groups is very important in the field of preparative chemistry as well as in degradation reactions. For example, in peptide-chemistry, penicillin-chemistry, cephalosporin-chemistry, alkaloid-chemistry, determination of the constitution of unknown compounds such as natural products, and the like.

The present invention is based on the observation that a carbonic acid ester, represented by formula (I) as shown below is a much more favorable agent for the temporary protection of amino and/or imino groups in the compound in comparison with the agents which have been conventionally employed in the art. For example, 1. the carbonic acid ester is present in stable oil or crystals and does not exhibit explosiveness, corrosiveness or irritativeness which are often exhibited by conventional agents. It is much more favorable and safe for handling in experimental as well as industrial use,
2. the carbonic acid ester can be easily prepared and
3. reacts rapidly with amino and/or imino group-containing organic compounds under milder reaction conditions to give protected amino and/or imino group-containing compounds. This undesired side reactions and by-products, often associated with conventional agents, can be minimized or in some case substantially avoided. In the reaction of carbonic acid esters with the amino and/or imino group-containing compounds, there may be produced a compound of the formula:

$R_2$ — OH, wherein $R_2$ is as defined below. This compound is substantially the sole by-product and is easily recovered in pure form from the reaction mixture by conventional means such as extraction. Further, the compound may be used repeatedly as a starting material without any further purification, for the preparation of the compound (I) of the present invention.

Accordingly, the present invention provides a process for the protection of amino and/or imino groups in an amino and/or imino group-containing compounds, which comprises reacting an amino and/or imino group-containing compound with a carbonic acid ester of the formula:

$R_1OCOOR_2$  (I).

wherein
$R_1$ is lower alkyl which may have substituents selected from the group consisting of halogen, lower alkoxy and aryloxy, or ar(lower)alkyl which may have substituents selected from the group consisting of lower alkoxy, halogen, nitro and cyano, and
$R_2$ is benzotriazolyl which may be substituted with halogen; or a group represented by the formula:

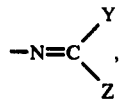

wherein
Y and Z are each aryl which may have substituents selected from the group consisting of halogen, lower alkoxy, nitro, cyano and halo(lower)alkyl, or an electron withdrawing group.

According to said reaction, the esterified carboxy group ($R_1OCO$—) in the carbonic acid ester (I) can be introduced to the amino and/or imino groups in the amino and/or imino group-containing compounds for the purpose of protecting said groups in said compound.

For this purpose, there may be used as starting material any desired amino and/or imino group-containing compound, especially an organic compound including all aliphatic, aromatic or a heterocyclic compounds, etc., each of which contains at least one amino or imino group in the molecule.

In this specification and claims, the term "lower" is intended to mean a group having 1 to 6 carbon atoms unless otherwise indicated.

A suitable example of lower alkyl for $R_1$ includes straight chain, branched or cyclic lower alkyls, having 1 to 6 carbon atoms. Examples of these lower alkyls include methyl, ethyl, propyl, isopropyl, butyl, isobutyl, tertbutyl, pentyl, neopentyl, tert-pentyl, hexyl, 1-cyclopropylethyl, cyclopropyl, cyclopentyl, cyclohexyl or the like. It is preferred that the lower alkyls have 2 to 5 carbon atoms and may optionally have at least one substituent selected from the group consisting of halogen (e.g., chlorine, bromine, fluorine, or iodine), lower alkoxy having 1 to 6 carbon atoms (e.g., methoxy, ethoxy, propoxy, isopropoxy, butoxy, tert-butoxy, pentyloxy, hexyloxy, etc.) and aryloxy having 6 to 10 carbon atoms (e.g., phenoxy, tolyloxy, xylyloxy, naphthyloxy, etc.).

A suitable example of ar(lower)alkyl for $R_1$ includes those groups having 7 to 10 carbon atoms such as benzyl, phenethyl, tolylmethyl, xylylmethyl, mesitylmethyl or the like. It is preferred that the ar(lower) alkyl have 7 to 8 carbon atoms and may optionally have at least one substituent selected from the group consisting of the aforementioned lower alkoxy, halogen, nitro and cyano.

A suitable example of aryl for Y and Z includes those having 6 to 10 carbon atoms such as phenyl, tolyl, xylyl, mesityl, cumenyl, naphthyl or the like, and these aryl groups may optionally have at least one substituent selected from the group consisting of the aforementioned halogen, lower alkoxy, nitro, cyano and halo (lower)alkyl (e.g., trichloromethyl, trifluoromethyl, etc.).

A suitable electron withdrawing group for Y and Z includes cyano, nitro, an acyl such as lower alkanoyl having 1 to 6 carbon atoms (e.g., formyl, acetyl, propionyl, butyryl, isobutyryl, valeryl, isovaleryl, pivaloyl, etc.), aroyl having 7 to 11 carbon atoms (e.g., benzoyl, toluoyl, xyloyl, naphthoyl, etc.), esterified carboxy, for example, lower alkoxycarbonyl having 2 to 7 carbon atoms (e.g., methoxycarbonyl, ethoxycarbonyl, propoxycarbonyl, isopropoxycarbonyl, butoxycarbonyl, isobutoxycarbonyl, tert-butoxycarbonyl, 1-cyclopropylethoxycarbonyl, cyclohexyloxycarbonyl, etc.), ar(lower)alkoxycarbonyl having 8 to 9 carbon atoms (e.g., benzyloxycarbonyl, phenethyloxycarbonyl, etc.) or aryloxycarbonyl having 7 to 8 carbon atoms (e.g., phenoxycarbonyl, tolyloxycarbonyl, etc.), carbamoyl, disubstituted carbamoyl, for example, di(lower)alkylcarbamoyl (e.g., dimethylcarbamoyl, diethylcarbamoyl, methylethylcarbamoyl, dipropylcarbamoyl, diisopropylcarbamoyl, dibutylcarbamoyl, etc.), lower alkylarylcarbamoyl (e.g., methylphenylcarbamoyl, ethylphenylcarbamoyl, etc.) or diarylcarbamoyl (e.g., diphenylcarbamoyl, ditolylcarbamoyl, etc.) or the like.

A suitable example of benzotriazolyl for $R_2$ may include 1H-benzotriazolyl or 2H-benzotriazolyl and these groups may contain at least one of the aforementioned halogens.

The present reaction may be conducted in a conventional manner (i.e. under conditions known in the art for using an esterified carboxy group to protect amino and/or imino groups in the compound). More particularly, the reaction may be conducted in a conventional solvent such as water, an alcohol (e.g., methanol, ethanol, propyl alcohol, butyl alcohol, tert-butyl alcohol, etc.), ethyl acetate, chloroform, dimethylformamide, methylene chloride, tetrahydrofuran, acetone or the like, or a mixture thereof, or other solvents which do not adversely affect the present reaction. The reaction may be optionally carried out in the presence of a base such as an inorganic base, for example, an alkali metal hydroxide (e.g., sodium hydroxide, potassium hydroxide, etc.), an alkaline earth metal hydroxide (e.g., calcium hydroxide, magnesium hydroxide, etc.), an alkali metal carbonate (e.g., sodium carbonate, potassium carbonate, etc.), an alkaline earth metal carbonate (e.g., calcium carbonate, magnesium carbonate, etc.), an alkali metal bicarbonate (e.g., sodium bicarbonate, potassium bicarbonate, etc.), or the like; an organic base, for example, an alkali metal acetate (e.g., sodium acetate, potassium acetate, etc.), trialkylamine (e.g., trimethylamine, triethylamine, etc.), triethanolamine, N,N-dimethylaniline, N,N-dimethylbenzylamine, N,N'-dimethylpiperazine, N-methylmorpholine, pyridine, quinoline, or the like; or a basic ion-exchange resin, or a mixture thereof.

The reaction temperature is not particularly limited, but the reaction is preferably carried out around room temperature.

The product having the protected amino and/or imino group(s) thus prepared can be isolated by a conventional method.

The protected amino and/or imino groups-containing compound can be used for further synthesis of known or new compounds in which it is necessary to protect the amino and/or imino groups in the compound in order to avoid any side-reaction, production of by-product and the like. The protected amino and/or imino groups-containing product thus synthesized, may be subsequently subjected releaved of the protective group (i.e., esterified carboxy group) in order to regenerate the free amino and/or imino group-containing compound. Such subsequent removal of the esterified carboxy type protective groups can be carried out by a conventional method.

The representative examples of the present carbonic acid ester (I) may be illustrated as follows.

2-Lower alkoxycarbonyloxyimino-2-cyanoacetamide (e.g., 2-ethoxycarbonyloxyimino-2-cyanoacetamide, 2-isobutoxycarbonyloxyimino-2-cyanoacetamide or 2-methoxycarbonyloxyimino-2-cyanoacetamide), di(lower)alkyl 2-lower alkoxycarbonyloxyiminomalonate (e.g., diethyl 2-ethoxycarbonyloxyiminomalonate or diethyl 2-tertbutoxycarbonyloxyiminomalonate), lower alkyl 2-lower alkoxycarbonyloxyimino-2-cyanoacetate (e.g., ethyl 2-ethoxycarbonyloxyimino-2-cyanoacetate, ethyl 2-isobutoxycarbonyloxyimino-2-cyanoacetate, ethyl 2-methoxycarbonyloxyimino-2-cyanoacetate or ethyl 2-tert-pentyloxycarbonyloxyimino-2cyanoacetate), lower alkyl 2-halo(lower)alkoxycarbonyloxyimino-2-cyanoacetate [e.g., ethyl 2-(2,2,2-trichloroethoxycarbonyloxyimino)-2-cyanoacetate], lower alkyl 2-ar(lower)alkoxycarbonyloxyimino-2-cyanoacetate (e.g., ethyl 2-benzyloxycarbonyloxyimino-2-cyanoacetate), lower alkyl 2-lower alkoxycarbonyloxyiminoacetoacetate (e.g., ethyl 2-tert-butoxycarbonyloxyiminoacetoacetate), di(lower)alkyl 2-lower alkoxy substituted ar(lower)alkoxycarbonyloxyiminomalonate [e.g., diethyl 2-(4-methoxybenzyloxycarbonyloxyimino)malonate], 2-lower alkoxycarbonyloxyimino-1-aryl(lower)alkane-1,3-dione (e.g., 2-tert-butoxycarbonyloxyimino-1-phenylbutane-1,3-dione), 1-lower alkoxycarbonyloxy-6-halobenzotriazole (e.g., 1-tertbutoxycarbonyloxy-6-chloro-1H-benzotriazole or 1-ethoxycarbonyloxy-6-chloro-1H-benzotriazole), 1-ar(lower) alkoxycarbonyloxybenzotriazole (e.g., 1-benzyloxycarbonyloxy-1H-benzotriazole), 2-lower alkoxycarbonyloxyimino-2-arylacetonitrile [e.g., 2-tert-butoxycarbonyloxyimino-2-phenylacetonitrile, 2-tert-butoxycarbonyloxyimino-2-(1-naphthyl) acetonitrile or 2-(1-cyclopropylethoxycarbonyloxyimino)-2-phenylacetonitrile], benzophenone O-lower alkoxycarbonyloxime (e.g., benzophenone O-tert-butoxycarbonyloxime), 2-halo(lower)alkoxycarbonyloxyimino-2-arylacetonitrile [e.g., 2-(2,2,2-trichloroethoxycarbonyloxyimino)-2-phenylacetonitrile], 2-lower alkoxy substituted or unsubstituted ar(lower)alkoxycarbonyloxyimino-2-arylacetonitrile [e.g., 2-(4-methoxybenzyloxycarbonyloxyimino)-2-phenylacetonitrile or 2-benzyloxycarbonyloxyimino-2-phenylacetonitrile], 2-lower alkoxycarboxyloxyimino-2-halogen substituted arylacetonitrile [e.g., 2-tert-butoxycarbonyloxyimino-2-(4-chlorophenyl)acetonitrile]or the like.

The carbonic acid ester of the formula (I) includes new and known compounds and the present invention also provides new carbonic acid esters and processes for the preparation thereof.

The new carbonic acid ester is represented by the following formula:

   I'.

wherein $R'_1$ is lower alkyl which may have substituents selected from the group consisting of halogen, lower alkoxy and aryloxy, or ar(lower)alkyl which may have substituents selected from the group consisting of lower alkoxy, halogen, nitro and cyano, and $R'_2$ is benzotriazolyl which may have halogen; or a group represented by the formula:

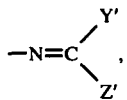

wherein
Y' and Z' are each aryl which may have substituents selected from the group consisting of halogen, lower alkoxy, nitro, cyano and halo(lower)alkyl; cyano; nitro, carbamoyl; esterified carboxy, lower alkanoyl, aroyl or disubstituted carbamoyl;
provided that when R'$_2$ is a group represented by the formula:

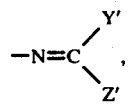

wherein
Y' and Z' are each cyano, nitro, carbamoyl or esterified carboxy,
R'$_1$ is ar(lower)alkyl having substituents selected from the group consisting of lower alkoxy, halogen, nitro and cyano;
and further provided that when R'$_1$ is lower alkyl and R'$_2$ is a group represented by the formula:

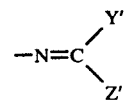

wherein
Y' is cyano and Z' is aryl, the number of carbon atoms of lower alkyl for R'$_1$ is 4 or 5.

Suitable examples of lower alkyl and ar(lower)alkyl for R'$_1$ and the substituents thereof may be the same as those as illustrated as examples for the definition for R$_1$, respectively.

Suitable examples of aryl, the substituents thereof, esterified carboxy, lower alkanoyl, aroyl and disubstituted carbamoyl for Y' and Z' may be the same as those illustrated as examples for the definitions of Y and Z. Suitable examples of benzotriazolyl and the substituent thereof for R'$_2$ may be the same as those illustrated as examples for the definition of R$_2$.

The new carbonic acid ester of the formula (I') can be prepared by reacting a haloformic acid ester of the formula:

X—COOR'$_2$     II.

wherein X is halogen and R'$_2$ is as defined above, with a hydroxy-compound of the formula:
R'$_1$ — OH     III.

wherein R'$_1$ is as defined above.

Suitable examples of halogen for X are the same as those illustrated as substituents for lower alkyl in the definition of R$_1$.

The reaction of the compound (II) with the compound (III) is usually carried out in a conventional solvent such as chloroform, tetrahydrofuran, ether, acetonitrile, ethyl acetate, acetone, benzene, n-hexane, petroleum ether, dioxane or any other organic solvent which does not adversely affect the reaction. The above reaction includes the use of these solvents individually or in combination. The reaction is preferably carried out in the presence of a base such as inorganic base, for example, alkali metal hydroxide (e.g., sodium hydroxide, potassium hydroxide, etc.), alkaline earth metal hydroxide (e.g., calcium hydroxide, magnesium hydroxide, etc.), alkali metal carbonate (e.g., sodium carbonate, potassium carbonate, etc.), alkaline earth metal carbonate (e.g., calcium carbonate, magnesium carbonate, etc.), alkali metal bicarbonate (e.g., sodium bicarbonate, potassium bicarbonate, etc.) or the like. In addition organic bases cn be used such as trimethylamine, triethylamine, triethanolamine, dimethylaniline, pyridine, quinoline, etc. These bases may be used alone or in combination. The reaction temperature is not critical, and the reaction is preferably carried out around room temperature or at a comparatively lower temperature.

Alternatively, the new carbonic acid ester (I') can be prepared by reacting a formic acid ester of the formula:

R'$_1$ — OCOX'     IV.

wherein R'$_1$ is as defined above and X' is halogen, with a compound of the formula:

R'$_2$ — OH     V.

wherein R'$_2$ is as defined above or a salt thereof.

Suitable examples of halogen of X' are the same as those illustrated as substituents for lower alkyl in the definition of R$_1$.

The suitable salts of compound (V) are the same as those examplified below for compound (VI).

In the present reaction, there can be employed similar solvents, bases and reaction temperature as those employed in the reaction of compound (II) with compound (III) as mentioned above. In addition, water or water mixed with the solvents mentioned above may also be used optionally depending on the properties of compound (IV).

Compound (I') can be also prepared by reacting a mixture of compounds (V) or a salt thereof, (III) and (VII) or a reactive equivalent thereof, in which the reaction may proceed via the same mechanism used for reacting compound (II) with compound (III) and/or reacting compound (IV) with compound (V).

Starting compound (II), for use in the above process, includes partially new compounds, which are represented by the following formula:

X — COOR'$_2$     II'.

wherein
X is as defined above and
R'$_2$ is benzotriazolyl which may have halogen; or a group represented by the formula:

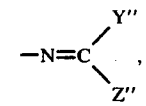

wherein
Y" is aryl which may have substituents selected from the group consisting of halogen, lower alkoxy, nitro, cyano and halo(lower)alkyl, cyano, nitro, carbamoyl, esterified carboxy, lower alkanoyl, aroyl or disubstituted carbamoyl and Z" is naphthyl, aryl having substituents selected from the group consisting of halogen, lower alkoxy, nitro, cyano and halo(lower)alkyl, lower alkanoyl, aroyl or disubstituted carbamoyl.

The new starting compound (II') can be prepared by reacting a compund of the formula:

R"₂ — OH        VI.

wherein R"₂ is as defined above, or a salt thereof with a carbonyl halide of the formula:

COX₂        VII.

wherein X is as defined above, or a reactive equivalent thereof.

A suitable salt of compound VI may include an alkali metal salt (e.g., sodium salt, potassium salt, etc.), alkaline earth metal salt (e.g., calcium salt, magnesium salt, etc.) or the like.

A suitable reactive equivalent of compound (VII) may include polymers of compound (VII), for example, the dimer (trichloromethyl chloroformate) or trimer [di(trichloromethyl) carbonate] of compound (VII), in which the suitable halogen for X is chlorine.

The reaction of compound (VI) with compound (VII) is usually carried out in a conventional solvent such as benzene, toluene, tetrahydrofuran, dioxane or any other organic solvent which does not adversely affect the reaction. The solvent may be used alone or in combination. The reaction is preferably carried out in the presence of a base such as an inorganic base for example, alkali metal hydroxide (e.g., sodium hydroxide, potassium hydroxide, etc.), alkaline earth metal hydroxide (e.g., calcium hydroxide, magnesium hydroxide, etc.), alkali metal carbonate (e.g., sodium carbonate, potassium carbonate, etc.), alkaline earth metal carbonate (e.g., calcium carbonate, magnesium carbonate, etc.), alkali metal bicarbonate (e.g., sodium bicarbonate, potassium bicarbonate, etc.) or an the like, or organic base (e.g., triethylamine, pyridine, dimethylaniline, etc.). The reaction temperature is not critical, and the reaction is preferably carried out under cooling or about room temperature.

In this process, compound (II'), may be isolated from the reaction mixture. In addition the reaction mixture per se can be preferably employed for the successive reaction with compound (III) without isolating compound (II').

Among the carbonic acid esters of formula (I) and the haloformic acid esters of formula (II), known compound also can be prepared according to substantially the same method as mentioned in the explanation of the processes for preparing the new carbonic acid ester (I') and the new haloformic acid ester of formula (II'), respectively.

The following examples are given for the purpose of illustrating the present invention:

EXAMPLE 1

[Process for the protection of amino and/or imino group(s)]

A. Triethylamine (0.42 ml.) was added to a suspension of D-2-(3-mesylaminophenyl)glycine (488 mg.) and diethyl 2-tertbutoxycarbonyloxyiminomalonate (770 mg.) in a mixture of tertbutyl alcohol (10 ml.) and water (10 ml.) The mixture was stirred for 1.5 hours at room temperature. Water and a sodium bicarbonate aqueous solution were added to the reaction mixture followed by ethyl acetate. The resulting mixture was adjusted to pH 7 with a citric acid aqueous solution. The aqueous layer was separated, washed with ethyl acetate, adjusted to pH 3.5 with a citric acid aqueous solution and extracted with ethyl acetate. The extract was washed with water, dried over magnesium sulfate and concentrated to give N-tert-butoxycarbonyl-D-2-(3-mesylaminophenyl)glycine (634 mg.).

| Nuclear Magnetic Resonance Spectrum [(CD₃)₂SO, δ] |
|---|
| ppm    7.00 - 7.60 (5H, m) |
|           5.11 (1H, d, J=8Hz) |
|           3.00 (3H, s) |
|           1.40 (9H, s) |

B. D-2-(3Mesylaminophenyl)glycine (2.44 g.) was suspended in a mixture of methanol: water (1:1) (volume ratio) (25 ml.) and dissolved by adding triethylamine (2.1 ml.). A solution of diethyl 2-tertbutoxycarbonyloxyiminomalonate (3.47 g.) in methanol (15 ml.) was added dropwise to the above solution over 10 minutes at 10 to 15° C. The resulting mixture was stirred for 2 hours at room temperature. The solvent was distilled off under reduced pressure to about 1/3 of the whole volume of the reaction mixture and water (30 ml.) plus a saturated sodium bicarbonate aqueous solution (10 ml.) were added to the residue. Ethyl acetate (40 ml.) and 0.5N hydrochloric acid (26 ml.) were added to the mixture and then the mixture was shaken. The aqueous layer was separated and ethyl acetate (100 ml.) was added thereto, the mixture was then adjusted to pH 7.20 with 0.5N hydrochloric acid (12 ml.). The aqueous layer was again separated, adjusted to pH 2.6 with 0.5N hydrochloric acid (27 ml.). This was followed by addition of a saturated sodium chloride aqueous solution and the aqueous layer was extracted twice with ethyl acetate (150 ml.). The extract was washed with a saturated sodium chloride aqueous solution, dried over magnesium sulfate and treated with activated charcoal. The solvent was distilled off under reduced pressure to give N-tert-butoxycarbonyl-D-2-(3-mesylaminophenyl)glycine (3.50 g.).

C. A solution of diethyl 2-tert-butoxycarbonyloxyiminomalonate (700 mg.) in acetone (5 ml.) was added dropwise to a solution of D-2-(3-mesylaminophenyl)glycine (488 mg.) and triethylamine (0.42 ml.) in a mixture of acetone (5 m.) and water (5 ml.) over 5 minutes at room temperature. The mixture was stirred for 2 hours at the same temperature. The reaction mixture was concentrated under reduced pressure. A sodium bicarbonate aqueous solution and water were added to the residue which brought the pH of the solution to about between 9 and 10. The solution was adjusted to pH 7 with a 0.5M citric acid aqueous solution and washed with ethyl acetate. This aqueous solution was adjusted to pH 3.5 with a 0.5M citric acid aqueous solution and extracted twice with ethyl acetate (30 ml.). The extract was washed with a sodium chloride aqueous solution and dried over magnesium sulfate. The solvent was distilled off under reduced pressure to give N-tert-butoxycarbonyl-D-2-(3-mesylaminophenyl)glycine (672 mg.), gummy.

D. A solution of diethyl 2-tert-butoxycarbonyloxyiminomalonate (1.9 g.) in tert-butyl alcohol (5 ml.) was added to a solution of L-isoleucine (656 mg.) in a 1N sodium hydroxide aqueous solution (5.0 ml). The mixture was stirred for 3 hours at room temperature. The tert-butyl alcohol was removed from the reaction mixture under reduced pressure and water was added to the residue. The mixture was washed with ether, adjusted to pH 3 with a 5% citric acid aqueous solution and extracted with ethyl acetate. The extract was washed with water, dried and concentrated to give N-tert-butoxycarbonyl-L-isoleucine (1.2 g.), oil.

E. Diethyl 2-tert-butoxycarbonyloxyiminomalonate (1.93 g.) was added to a solution of $N^G$-nitro-L-arginine (1.1 g.) and sodium bicarbonate (0.63 g.) in a mixture of water (50 ml.) and tert-butyl alcohol (20 ml.). The mixture was stirred for 3 hours at room temperature. The reaction mixture was adjusted to pH 7.0 with a citric acid aqueous solution, washed with ethyl acetate, adjusted to pH 3 with a citric acid aqueous solution and extracted with ethyl acetate (100 ml.). The extract was washed with water, dried over magnesium sulfate and concentrated under reduced pressure. The residue was crystallized with a mixture of ethyl acetate and petroleum ether and the precipitates were collected by filtration to give $N^\alpha$-tert-butoxycarbonyl-$N^G$-nitro-L-arginine (1.1 g.), mp 114° to 116° C (dec.).

F. L-Phenylalanine (330 mg.) and sodium bicarbonate (202 mg.) were dissolved in water (10 ml.) under heating and allowed to stand. A solution of diethyl 2-(4-methoxybenzyloxycarbonyloxyimino)malonate (1.0 g.) in tert-butyl alcohol (10 ml.) was added to the solution with stirring at room temperature and water (10 ml.) was added thereto, the mixture was then stirred for 2 hours at room temperature. The reaction mixture was brought to pH 9 by adding water (20 ml.) and saturated sodium bicarbonate aqueous solution (10 ml.), and water (10 ml.) was added thereto. The resulting mixture was then washed twice with ethyl acetate (20 ml.). The aqueous layer was adjusted to pH 7 with a 10% citric acid aqueous solution, washed twice with ethyl acetate (30 ml.), adjusted to pH 3.5 with a 10% citric acid aqueous solution and extracted three times with ethyl acetate (30 ml.). The extract was washed with a sodium chloride aqueous solution and dried over magnesium sulfate. The solvent was distilled off under reduced pressure to give N-(4-methoxybenzyloxycarbonyl)-L-phenyalanine (410 mg.), oil.

G. A solution of ethyl 2-tert-butoxycarbonyloxyiminoacetoacetate (646 mg.) in a mixture of tert-butyl alcohol (5 ml.) and water (5 ml.) was added at once to a solution of L-phenylalanine (330 mg.) and triethylamine (0.28 ml.) in a mixture of tert-butyl alcohol (8 ml.) and water (8 ml.) at room temperature. The mixture was stirred for 2 hours at room temperature. Water (100 ml.) was added to the reaction mixture and the mixture was adjusted to pH 7 with a 0.5M citric acid aqueous solution and washed twice with ethyl acetate (40 ml). The aqueous layer was adjusted to pH 3 with a 0.5M citric acid aqueous solution, followed by addition of a sodium chloride aqueous solution, and extracted twice with ethyl acetate (40 ml.). The extract was washed with water and dried. The solvent was distilled off under reduced pressure to give N-tert-butoxycarbonyl-L-phenylalanine (286 mg.).

H. Triethylamine (1.68 ml.) was added to a suspension of L-alanine (0.89 g.) in a mixture of water (5 ml.) and tert-butyl alcohol (5 ml.) to give homogeneous solution. Diethyl 2-tert-butoxycarbonyloxyiminomalonate (4.0 g.) was added to the solution and the mixture was stirred for 1 hour at room temperature. tert-Butyl alcohol was distilled off from the reaction mixture under reduced pressure and ether and a 5% sodium bicarbonate aqueous solution were added to the residue. The resulting mixture was adjusted to pH 7 with a citric acid aqueous solution. The aqueous layer was separated and ethyl acetate was added thereto. The mixture was then adjusted to pH 3 with a citric acid aqueous solution. The mixture was adequately shaken and the ethyl acetate layer was separated, washed with water and dried. The solution was concentrated under reduced pressure and the residue was recrystallized from a mixture of ether and petroleum ether to give N-tert-butoxycarbonyl-L-alanine (1.59 g.), mp 82° to 84° C.

I. A suspension of 1-tert-butoxycarbonyloxy-6-chloro-1H-benzotriazole (2.7 g.), L-isoleucine (1.3 g) and triethylamine (3.5 ml.) in a mixture of water (8 ml.) and tert-butyl alcohol (12 ml.) was stirred for 2 hours at 60° to 62° C. tert-Butyl alcohol was distilled off from the reaction mixture under reduced pressure and water (15 ml.) was added to the residue. The mixture was adjusted to pH 3 with a citric acid aqueous solution under ice-cooling and extracted with ethyl acetate. The extract was then washed with water and a saturated sodium chloride aqueous solution. The thus formed precipitates were filtered off and then the filtrate was dried over magnesium sulfate. The solution was concentrated and a mixture of ether and petroleum ether (1:1) was added to the residue. An insoluble material was filtered off and the filtrate was concentrated under reduced pressure to give N-tert-butoxycarbonyl-L-isoleucine (2.4 g.), oil.

Infrared Absorption Sprectrum (Film): 2980, 1725 (shoulder), 1710, 1165 cm$^{-1}$.

J. A solution of diethyl 2-tert-butoxycarbonyloxyiminomalonate (4.5 g.) in tert-butyl alcohol (40 ml.) was added at once to a solution of D-2-(3-dimesylaminophenyl)glycine (3.22 g.) and sodium bicarbonate (1.26g.) in a mixture of tert-butyl alcohol (80 ml.) and water (120 ml.) under ice-cooling and stirring. After stirring for 1.5 hours at room temperature, an insoluble material was filtered off. The filtrate was adjusted to pH 7.5 with a 0.2M citric acid aqueous solution and tert-butyl alcohol was distilled off under reduced pressure. The residue was washed with ether and adjusted to pH 3 with a 0.2M citric acid aqueous solution. The aqueous solution was saturated with sodium chloride and extracted with ethyl acetate. The extract was washed with a saturated sodium chloride aqueous solution and dried, and the solvent was distilled off under reduced pressure to give N-tert-butoxycarbonyl-D-2-(3-dimesylaminophenyl)-glycine (2.1 g.), foamy solid.

| Nuclear Magnetic Resonance Spectrum [$(CD_3)_2SO$, $\delta$] | |
|---|---|
| ppm | 7.50 (4H, m) |
| | 5.20 (1H, d) |
| | 3.33 (6H, s) |
| | 1.40 (9H, s) |

K. N-tert-Butoxycarbonyl-L-phenylalanine was obtained according to a method similar to that of Example 1 (G) by using L-phenylalanine and 2-tert-butoxycarbonyloxyimino-1-phenylbutane-1,3-dione.

L. N-Benzyloxycarbonyl-L-phenylalanine was obtained according to a method similar to that of Example 1 (G) by using L-phenylalanine and ethyl 2-benzyloxycarbonyloxyimino-2-cyanoacetate.

M. 6-Benzyloxycarbonylaminopenicillanic acid was obtained according to a method similar to that of Example 1 (G) by using 6-aminopenicillanic acid and ethyl 2-benzyloxycarbonyloxyimino-2-cyanoacetate.

N. 2-(4-Methoxybenzyl)oxycarbonyloxyimino-2-phenylacetonitrile (1.55 g.) was added to a solution of L-phenylalanine (826 mg.) and triethylamine (0.75 ml.) in a mixture of methanol (10 ml.), dioxane (1.5 ml.) and water (7.5 ml.) at room temperature the resulting mixture was stirred for 2 hours at room temperature. The reaction mixture was concentrated and benzene and a sodium bicarbonate aqueous solution were added to the residue. After shaking the resultant mixture, the aqueous layer was separated from the mixture, washed with ether, acidified with hydrochloric acid and extracted with ethyl acetate. The extract was washed with water, dried and concentrated. N-Hexane was added to the residue, and the precipitated crystals were collected by filtration and dried to give N-(4-methoxybenzyl)oxycarbonyl-L-phenylalanine (1.064 g.), mp 87° to 88° C.

O. 2-tert-Butoxycarbonyloxyimino-2-phenylacetonitrile (1.25 g.) was added to a solution of L-proline (575 mg.) and triethylamine (0.7 ml.) in a mixture of methanol (7.5 ml.), dioxane (2.5 ml.) and water (5.0 ml.) at room temperature. The reaction mixture was concentrated under reduced pressure and benzene and water were added to the residue. After shaking the resultant mixture, the aqueous layer was separated from the mixture, washed with benzene, acidified with hydrochloric acid, and extracted with ethyl acetate. The extract was washed with water, dried over magnesium sulfate and concentrated. A mixture of ether and n-hexane was added to the residue and the residue was added a mixture of ether and n-hexane and the precipitated crystals were collected by filtration and dried to give N-tert-butoxycarbonyl-L-proline (845 mg.), mp (845 mg.), mp 133° to 134° C.

P. According to a method similar to that of Example 1 (O), N-tert-butoxycarbonyl-L-leucine hemihydrate (899 mg.), mp 78° to 84° C, was obtained by using L-leucine (656 mg.) and 2-tertbutoxycarbonyloxyimino-2-phenylacetonitrile (1.35 g.) as starting materials.

Q. According to a method similar to that of Example 1 (O), N-tert-butoxycarbonyl-L-methionine dicyclohexylamine salt (1.768 g.), mp 137° to 139° C, was obtained by using L-methionine (746 mg.) and 2-tert-butoxycarbonyloxyimino-2-phenylacetonitrile (1.35 g.) as starting materials.

R. According to a method similar to that of Example 1 (O), N-tert-butoxycarbonyl-L-phenylalanine dicyclohexylamine salt (1.463 g.) mp 222° to 223° C (dec.), was obtained by using L-phenylalanine (826 mg.) and 2-tert-butoxycarbonyloxyimino-2-phenylacetonitrile (1.25 g.) as starting materials.

S. According to a method similar to that of Example 1 (O), N-tert-butoxycarbonyl-L-asparagine (918 mg.), mp 166° to 167° C (dec.), was obtained by using L-asparagine hydrate (0.75 g.) and 2-tert-butoxycarbonyloxyimino-2-phenylacetonitrile (1.85 g.) as starting materials.

T. According to a method similar to that of Example 1 (O), $N^\alpha$-tert-butoxycarbonyl-$N^G$-nitro-L-arginine (2.56 g.), mp 123 to 125° C, was obtained by using $N^G$-nitro-L-arginine (2.20 g.) and 2-tert-butoxycarbonyloxyimino-2-phenylacetonitrile (2.71 g.) as starting materials.

U. According to a method similar to that of Example 1 (O), N-tert-butoxycarbonyl-L-threonine dicyclohexylamine salt (5.50 g.), mp 152° to 153° C, was obtained by using L-threonine (2.4 g.) and 2-tert-butoxycarbonyloxyimino-2-phenylacetonitrile (5.4 g.) as starting materials.

V. According to a method similar to that of Example 1 (O), N-tert-butoxycarbonylglycine (1.523 g.), mp 86.5° to 87.5° C, was obtained by using glycine (0.75 g.) and 2-tert-butoxycarbonyloxyimino-2-phenylacetonitrile (2.71 g.) as starting materials.

W. According to a method similar to that described in the foregoing Examples 1 (A) and 1 (V), the process for the protection of amino and/or imino groups gives similar results and is carried out by using the following various carbonic acid esters.

1. 2-Ethoxycarbonyloxyimino-2-cyanoacetamide, mp 194° to 196° C.
2. Diethyl 2-ethoxycarbonyloxyiminomalonate, oil.
3. Ethyl 2-ethoxycarbonyloxyimino-2-cyanoacetate, oil.
4. 2-Isobutoxycarbonyloxyimino-2-cyanoacetamide, mp 156 to 158° C.
5. Ethyl 2-isobutoxycarbonyloxyimino-2-cyanoacetate, mp 60° to 62° C.
6. 2-Methoxycarbonyloxyimino-2-cyanoacetamide, mp 174° to 175° C (dec.).
7. Ethyl 2-methoxycarbonyloxyimino-2-cyanoacetate, mp 69° to 71° C.
8. Ethyl 2-(2,2,2-trichloroethoxycarbonyloxyimino)-2-cyanoacetate, mp 51° to 53° C.
9. Ethyl 2-tert-pentyloxycarbonyloxyimino-2-cyanoacetate, oil.

Infrared Absorption Spectrum: 1810, 1740 $cm^{-1}$.

10. 1-Ethoxycarbonyloxy-6-chloro-1H-benzotriazole, mp 160° to 162° C.
11. 1-Benzyloxycarbonyloxy-1H-benzotriazole, mp 130° to 131° C.
12. Benzophenone O-tert-butoxycarbonyloxime, mp 131° to 133° C.
13. 2-tert-Butoxycarbonyloxyimino-2-(4-chlorophenyl)acetonitrile, mp 91° to 92° C.
14. 2-Benzyloxycarbonyloxyimino-2-phenylacetonitrile, mp 73° to 75° C.
15. 2-tert-Butoxycarbonyloxyimino-2(1-naphthyl)acetonitrile, mp 90° to 92° C.
16. 2-(1-Cyclopropylethoxycarbonyloxyimino)-2-phenylacetonitrile, mp 65 to 67° C.
17. 2-(2,2,2-Trichloroethoxycarbonyloxyimino)-2-phenylacetonitrile, mp 82° to 84° C.

EXAMPLE 2 [PREPARATION OF CARBONIC ACID ESTERS]

A. Benzene (20 ml.) was added to a solution of phosgene 2.5 g.) in benzene (11.4 ml.). A solution of diethyl 2-hydroxyiminomalonate (4.73 g.) and N,N-dimethylaniline (3.03 g.) in benzene (30 ml.) was added dropwise to the solution over 40 minutes at 5° C in a nitrogen stream. The mixture was stirred for 1 hour at the same temperature and overnight at room temperature. A solution of 4-methoxybenzylalcohol (3.11 g.) and pyridine (4.04 ml.) in benzene (30 ml.) was added dropwise the the resultant mixture containing diethyl 2-chlorocarbonyloxyiminomalonate over a period of 40 minutes at 5° C. The mixture was stirred for 2 hours at the same temperature, for 3 hours at room temperature and allowed to stand overnight. Cold water (100 ml.) was added to the reaction mixture to dissolve an insoluble material and cooled 1N-hydrochloric acid (20 ml.) was added thereto, after which the mixture was shaken. The organic layer was then washed 3 times with 1N hydrochloric acid (20 ml.), 3 times with a 5% sodium carbonate aqueous solution (20 ml.) and a sodium chloride aqueous solution, and then dried over magnesium sulfate. After drying, the solvent was distilled off to give diethyl 2-(4-methoxybenzyloxycarbonyloxyimino)malonate (6.89 g.), a pale brown oil, which was solidified on standing at ambient temperature.

Nuclear Magnetic Resonance Spectrum (CCl$_4$, δ)
ppm    6.88, 7.38 (4H, ABq, J=9.0 Hz)
       5.23 (2H, s)
       4.39 (4H, q, J=7.1 Hz)
       3.80 (3H, s)
       1.37 (3H, t, J=7.1 Hz)
       1.33 (3H, t, J=7.1 Hz)

B. A solution of ethyl 2-hydroxyiminoacetoacetate (3.98 g.) and pyridine (1.98 g.) in benzene (25 ml.) was added dropwise to a solution of phosgene (2.48 g.) in benzene (30 ml.) for 30 minutes at 4° to 5° C. After stirring for 1 hour at the same temperature, the mixture was stirred for 1 hour at room temperature and allowed to stand overnight. A solution of tert-butyl alcohol (3.7 g.) and pyridine (3.96 g.) in benzene (25 ml.) was added dropwise for 30 minutes at 5° to 7° C. to the resultant solution containing ethyl 2-chlorocarbonyloxyiminoacetoacetate. After stirring for 1 hour at the same temperature, the reaction temperature was slowly elevated to room temperature, after which the mixture was stirred for 6 hours at the same temperature and allowed to stand overnight. A precipitate as dissolved by adding about the same volume of water as that of the organic layer to the reaction mixture. The aqueous layer was then separated. The organic layer was then washed with a 0.5M citric acid aqueous solution, a 5% sodium carbonate aqueous solution and a sodium chloride aqueous solution, and dried over magnesium sulfate. After drying, the solvent was distilled off to give ethyl 2-tert-butoxycarbonyloxyiminoacetoacetate (3.7 g.), oil.

Infrared Absorption Spectrum (Film): 1780, 1730, 1690 cm$^{-1}$.

Nuclear Magnetic Resonance Spectrum (CCl$_4$, δ)
ppm    4.34 (3H, q)
       2.48 (3H, s)
       1.57 (9H, s)
       1.37 (3H, t)

C. A solution of 2-hydroxyimino-1-phenylbutane-1,3-dione (3.82 g.) and pyridine (1.62 ml.) in benzene (30 ml.) was added dropwise to a solution of phosgene (1.98 g.) in benzene (25 ml.) for 40 minutes at 5° to 9° C. After stirring for 1 hour at the same temperature, the mixture was allowed to stand overnight. A solution of tert-butyl alcohol (2.96 g.) and pyridine (3.16 g.) in benzene (30 ml.) was added dropwise for 30 minutes at 5° C. to the resultant solution containing 2-chlorocarbonyloxyimino-1-phenylbutane-1,3-dione. After stirring for 1 hour at the same temperature, the mixture was stirred for 6 hours at room temperature, after which the mixture was allowed to stand overnight. Cooled water (100 ml.) was added to the reaction mixture and the organic layer was then washed with water, a 0.5M citric acid aqueous solution (20 ml.) (4 times) and a 5% sodium carbonate aqueous solution (20 ml.) (4 times) until the aqueous layer became almost colorless. The organic layer was further washed with a sodium chloride aqueous solution and then dried over magnesium sulfate. After drying, the solution was treated with activated charcoal and the solvent was distilled off to give an oil (3.48 g.). The oil was partly crystallized by allowing it to stand and ether was then added to the mixture to precipitate crystals. The precipitates were collected by filtration and recrystallized from a mixed solvent of carbon tetrachloride and petroleum ether to give 2-tert-butoxycarbonyloxyimino-1-phenylbutane-1,3-dione (350 mg.), mp 90° to 103° C (dec.).

Infrared Absorption Spectrum (Nujol): 1785, 1700, 1680 cm$^{-1}$.

Analysis: $C_{15}H_{17}NO_5$: Calcd.: C, 61.85, H, 5.88, N, 4.81 Found: C, 62.00, H, 5.92, N, 4.98

D. A solution of phosgene (5g.) in benzene (23.5 ml.) was added dropwise under ice-cooling to a suspension of 1-hydroxy-6-chloro-1H-benzotriazole (8.5 g.) and pyridine (3.9 g.) in benzene (50 ml.). The mixture was stirred for 30 minutes at the same temperature and allowed to stand overnight. A solution of tert-butyl alcohol (3.7 g.) and pyridine (4.0 g.) in benzene (50 ml.) was added dropwise for 20 minutes under ice-cooling to the resultant solution containing 1-chlorocarbonyloxy-6-chloro-1H-benzotriazole. The resultant mixture was stirred for 2 hours at the same temperature and allowed to stand overnight. The reaction mixture was filtered and the filtrate was concentrated. Ether and petroleum ether were added to the residue to pulverize the residue and the resultant crystals were collected by filtration to give 1-tert-butoxycarbonyloxy-6-chloro-1H-benzotriazole (5.3 g.). The mother liquor was concentrated to give the same desired compound (0.6 g.). Both quantities of crystals were mixed and dissolved in benzene. The resultant solution was then washed with a sodium bicarbonate aqueous solution and water and then dried. The solvent was removed by distillation to give the desired compound (3.2 g.), powder, mp 98° to 100° C (dec.).

Analysis: $C_{11}H_{12}N_3O_3Cl$ Calcd.: C, 48.98, H, 4.48, N, 15.58, Cl, 13.14 Found: C, 49.25, H, 4.32, N, 15.88, Cl, 13.36

E. A solution of 2-hydroxyimino-2-phenylacetonitrile (7.3 g.) and dimethylaniline (6.0 g) in a mixture of benzene (50 ml) and dioxane (5 ml.) was added dropwise to a solution of phosgene (5.5 g.) in benzene (50 ml.) over 1 hour at 3° to 5° C. The mixture was stirred for 3.5 hours at the same temperature and allowed to stand overnight. A solution of tert-butyl alcohol (7.4 g.) and pyridine (5.0 ml.) in benzene (20 ml.) was added dropwise for 1 hour under ice-cooling to the resultant solution containing 2-chlorocarbonyloxyimino2-phenylacetonitrile. The resultant mixture was stirred for 4 hours at the same temperature, and pyridine (3.0 ml.) was added dropwise thereto. The mixture was then stirred for 1 hour at room temperature and allowed to stand overnight. Water was added thereto and the organic layer was separated. The organic layer was then washed with 1N hydrochloric acid (3 times), a sodium chloride aqueous solution, a sodium bicarbonate aqueous solution (twice) and a sodium chloride aqueous solution (twice) and concentrated. The residue was allowed to stand to obtain crystals. The crystals were triturated in aqueous methanol, collected by filtration, washed with n-hexane and dried to give 2-tert-butoxycarbonyloxyimino-2-phenylacetonitrile (7.0 g.), mp 84° to 86° C.

Infrared Absoprtion Spectrum (Nujol): 1785 cm⁻¹.

Nuclear Magnetic Resonance Spectrum (CDCl₃, δ)
ppm     7.3 - 8.1 (5H, m)
        1.60 (9H, s)

F. A solution of 2-hydroxyimino-2-phenylacetonitrile (7.3 g.), dimethylaniline (6.0 g.) and tert-butyl alcohol (3.7 g.) in benzene (50 ml.) was added dropwise to a solution of phosgene (5.0 g.) in benzene (50 ml.) for 30 minutes under ice-cooling. A solution of pyridine (4.0 ml.) in benzene (20 ml.) was added dropwise to the mixture. The resultant mixture was stirred for 1 hour at the same temperature and allowed to stand overnight. Water and benzene were added to the reaction mixture and an insoluble material was filtered off. The organic layer was then washed with 1N hydrochloric acid, water, a sodium bicarbonate aqueous solution and water, and dried over magnesium sulfate. The solvent was distilled off and n-hexane and a small amount of methanol were added to the residue. An insoluble material was filtered off and the filtrate was concentrated. Methanol was added to the residue and the mixture was allowed to stand. The precipitates were collected by filtration to give 2-tert-butoxycarbonyloxyimino-2-phenylacetonitrile (3.5 g.), Mp 83° to 85° C. Water was added to the mother liquor and the mixture was allowed to stand. The precipitates were collected by filtration to give the desired compound (1.5 g.). Total yield (5.0 g.).

G. A solution of 2-hydroxyimino-2-phenylacetonitrile (14.6 g.) and dimethylaniline (13.2 g.) in a mixture of acetone (5 ml.) and benzene (80 ml.) was added to a solution of trichloromethyl chloroformate (phosgene dimer) (6.7 ml.) in benzene (30 ml.) under ice-cooling. The mixture was stirred for 6 hours at the same temperature and allowed to stand overnight. A mixture of tert-butyl alcohol (11.1 g.), pyridine (16.0 ml.) and benzene (20 ml.) was added dropwise, under ice-cooling, to the resultant mixture containing 2-chlorocarbonyloxyimino-2-phenyl-acetonitrile. The mixture was stirred for 7 hours at room temperature and allowed to stand overnight. The reaction mixture was treated as described in the above Examples 2(A) to 2(F) to give 2-tert-butoxycarbonyloxyimino-2-phenylacetonitrile (17.0 g.), mp 84° to 86° C.

H. A solution of dimethylaniline (6.0 ml.) in benzene (15 ml.) was added dropwise to a suspension of 2-hydroxyimino-2-phenylacetonitrile (7.3 g.) and phosgene (5.0 g.) in benzene (50 ml.) for 40 minutes under ice-cooling. The mixture was stirred for 2 hours at the same temperature and allowed to stand overnight. A solution of 4-methoxybenzyl alcohol (6.9 g.) and pyridine (4.0 ml.) in benzene (20 ml.) was added dropwise, for 30 minutes under ice-cooling to the mixture containing 2-chlorocarbonyloxyimino-2-phenylacetonitrile. The mixture was stirred for 7 hours at room temperature. The reaction mixture was then washed with water, 1N hydrochloric acid, water, a sodium bicarbonate aqueous solution and water, and dried over magnesium sulfate. The solution was concentrated and the residual crystals were triturated in n-hexane and collected by filtration. The crystals were recrystallized from a mixture of ethyl acetate and n-hexane to give 2-(4-methoxybenzyl)oxycarbonyloxyimino-2-phenylacetonitrile (3.1 g.). Mp 112° to 113° C. The mother liquor was concentrated to give the desired compound (2.4 g.). Total yield (5.5 g.).

Infrared Absorption Spectrum (Nujol): 1785 cm⁻¹.

Nuclear Magnetic Resonance Spectrum (CDCl₃, δ)
ppm     6.8 - 8.0 (9H, m)
        5.30 (2H, s)
        3.80 (3H, s)

Analysis: $C_{17}H_{14}O_4N_2$: Calcd.: C, 65.79, H, 4.54, N, 9.03; Found: C, 65.99, H, 4.38, N, 9.03.

I. A solution of 2-hydroxyimino-2-phenylacetonitrile (14.6 g) and dimethylaniline (13.2 g.) in a mixture of benzene (80 ml.) and dioxane (8 ml.) was added to a solution of trichloromethyl chloroformate (phosgene dimer) (11 g.) in benzene (50 ml.) under ice-cooling. The and the mixture was stirred for 3 hours at the same temperature and allowed to stand overnight. A solution of tert-butyl alcohol (14.8 g.) and pyridine (16.0 ml.) in benzene (20 ml.) was added dropwise, under ice-cooling, to the mixture containing 2-chlorocrabonyloxyimino-2-phenylacetonitrile. The reaction mixture was stirred for 6 hours and the reaction temperature was gradually elevated to room temperature and allowed to stand overnight. Water was added to the reaction mixture and the organic layer was separated. The organic layer was then washed with 1N hydrochloric acid, a sodium chloride aqueous solution, a sodium bicarbonate aqueous solution and water and then dried. The solvent was distilled off and methanol was added to the residue. The mixture was cooled with ice-water and the precipitates were collected by filtration and washed with a small amount of cooled methanol to give 2-tert-butoxycarbonyloxyimino-2-phenylacetonitrile (9.5 g.). The desired compound (9.4 g.) was further obtained from the mother liquor. Amounts of the desired compounds obtained above were combined and recrystallized from methanol to give the pure compound (14.6 g.), mp 84° to 86° C.

J. A solution of benzophenone oxime (9.85 g.) and dimethylaniline (6.6 g.) in a mixture of benzene (50 ml.) and dioxane (10 ml.) was added dropwise to a solution of trichloromethyl chloroformate (phosgene dimer) (5.5 g.) in benzene (15 ml.) under ice-cooling. The resultant mixture was stirred for 1 hour at the same temperature, for 2 hours at room temperature and then allowed to stand overnight. A solution of tert-butyl alcohol (5.6 g.) and pyridine (6.0 ml.) in benzene (20 ml.) was added dropwise, under ice-cooling to the resultant mixture containing benzophenone O-chlorocarbonyloxime. The mixture was stirred for 6 hours at the same temperature and allowed to stand overnight. The reaction mixture was then washed with water, 1N hydrochloric acid, water, a sodium bicarbonate aqueous solution and water, and dried over magnesium sulfate. The solvent was distilled off and petroleum ether was added to the resulting crystals. The crystals were collected by filtration and dried to give benzophenone O-tert-butoxycarbonyloxime (10.5 g.), mp 126° to 133° C. A small amount of the crystals was recrystallized from a mixture of toluene and petroleum ether to give the pure compound, mp 131° to 133° C.

Infrared Absorption Spectrum (Nujol): 1770 cm⁻¹.

| Nuclear Magnetic Resonance Spectrum (CDCl$_3$, δ) | |
|---|---|
| ppm | 7.17 - 7.65 (10H, m) |
| | 1.48 (9H, s) |

K. A suspension of 2-hydroxyimino-2-(4-chlorophenyl)acetonitrile (6.75 g.) and dimethylaniline (4.5 g.) in a mixture of dichloromethane (70 ml.), dioxane (10 ml.) and tetrahydrofuran (10 ml.) was added dropwise to a solution of trichloromethyl chloroformate (phosgene dimer) (16 g.) in benzene (22 ml.) under ice-cooling. The mixture was stirred for 5 hours at the same temperature and allowed to stand overnight. A solution of tertbutyl alcohol (8.9 g.) and pyridine (9.6 ml.) in dichloromethane (20 ml.) was added dropwise, under ice-cooling, to the resultant mixture containing 2-chlorocarbonyloxyimino-2-(4-chlorophenyl)acetonitrile. The mixture was stirred for 5 hours at the same temperature and allowed to stand for 48 hours. The reaction mixture was then washed with water, 1N hydrochloric acid, water, a sodium bicarbonate aqueous solution and water, and dried over magnesium sulfate. The solvent was distilled off and n-hexane was added to the residue. An insoluble material was filtered off and the filtrate was concentrated. Petroleum ether was added to the residue and the mixture was allowed to stand to precipitate crystals. The crystals were dissolved in hot petroleum ether and the solution was filtered. The filtrate was cooled to precipitate crystals and the crystals were collected by filtration to give 2-tert-butoxycarbonyloxyimino-2-(4-chlorophenyl)acetonitrile (1.6 g.). These crystals were recrystallized from methanol to give the pure compound (0.7 g.), mp 91° to 92° C.

Infrared Absorption Spectrum (Nujol): 1790 cm$^{-1}$.

| Nuclear Magnetic Resonance Spectrum (CDCl$_3$, δ) | |
|---|---|
| ppm | 7.90 (2H, ABq, J=4.5Hz) |
| | 7.50 (2H, ABq, J=4.5Hz) |
| | 1.63 (9H, s) |

L.:
1. Preparation of the starting compound 2-(1-naphthyl)acetonitrile (16.7 g.) was added to a solution of sodium hydroxide (4.2 g.) in methanol (80 ml.). Gaseous methyl nitrite which was prepared by adding a solution of concentrated sulfuric acid (5 ml.) in water (10 ml.) to a solution of sodium nitrite (8.3 g.) in a mixture of methanol was introduced, under ice-cooling, and water (5 ml.). The mixture was stirred for 4 hours at the same temperature and the reaction mixture was treated by a conventional method to give 2-hydroxyimino-2-(1-naphthyl)acetonitrile (7.1 g.), oil.

Infrared Absorption Spectrum (Film): 1700 cm$^{-1}$.

2. Preparation of the desired compound

A solution of 2-hydroxyimino-2-(1-naphthyl)acetonitrile (7.0 g.) and dimethylaniline (12.0 g.) in toluene (100 ml.) was added dropwise, under ice-cooling, to a solution of trichloromethyl chloroformate (phosgene dimer) (3.56 g.) in benzene (30 ml.). The mixture was stirred for 3 hours at the same temperature and allowed to stand overnight. A solution of tert-butyl alcohol (11.1 g.) and pyridine (12 ml.) in toluene (20 ml.) was added dropwise, under ice-cooling, to the resultant mixture containing 2-chlorocarbonyloxyimino-2-(1-naphthyl)acetonitrile. The mixture was stirred for 6 hours at the same temperature and allowed to stand overnight. The reaction mixture was then washed with water, 1N hydrochloric acid, water, a sodium bicarbonate aqueous solution and water, and dried over magnesium sulfate. The solution was concentrated under reduced pressure and n-hexane and methanol were added to the residue. The mixture was allowed to stand in a refrigerator and the precipitated crystals were collected by filtration and recrystallized twice from methanol to give 2-tert-butoxycarbonyloxyimino-2-(1-naphthyl)acetonitrile (3.3 g.), mp 90° to 92° C.

Analysis: C$_{17}$H$_{16}$O$_3$N$_2$: Calcd.: C, 68.90, H, 5.44, N, 9.46; Found: C, 68.85, H, 5.38, N, 9.40.

Infrared Absorption Spectrum (Nujol): 1790 cm$^{-1}$.

M. A solution of 2-hydroxyimino-2-phenylacetonitrile (2.2 g.) and dimethylaniline (1.80 g.) in a mixture of benzene (25 ml.) and dioxane (3 ml.) was added dropwise to a solution of trichloromethyl chloroformate (phosgene dimer) (1.5 g.) in benzene (20 ml.) under ice-cooling. The mixture was stirred for 3 hours at the same temperature and allowed to stand overnight. A solution of 1-cyclopropylethanol (1.4 g.) and pyridine (1.2 ml.) in benzene (10 ml.) was added dropwise, under ice-cooling, to the resultant mixture containing 2-chlorocarbonyloxyimino-2-phenylacetonitrile. The mixture was stirred for 2 hours at the same temperature, for 4 hours at room temperature and allowed to stand overnight. The reaction mixture was then washed with 1N hydrochloric acid, water, a sodium bicarbonate aqueous solution and water, and dried over magnesium sulfate. The solvent was distilled off and a small amount of methanol to the oily residue was added a small amount of methanol. The mixture was allowed to stand in a refrigerator and the precipitated crystals were collected by filtration and recrystallized from methanol to give 2-(1-cyclopropylethoxycarbonyloxyimino)-2-phenylacetonitrile (0.7 g.), mp 65° to 67° C.

Infrared Absorption Spectrum (Nujol): 1785 cm$^{-1}$.

Analysis: C$_{14}$H$_{14}$O$_3$N$_2$: Calcd.: C, 65.10, H, 5.46, N, 10.85; Found: C, 65,07, H, 5.15, N, 10.84.

N. The following compounds were obtained according to a method similar to those described in Examples 2(A) to 2(M).

1. 1-Ethoxycarbonyloxy-6-chloro-1H-benzotriazole, mp 160 to 162° C.

2. 1-Benzyloxycarbonyloxy-1H-benzotriazole, mp 130° to 131° C.

3. 2-Benzyloxycarbonyloxyimino-2-phenylacetonitrile, mp 73° to 75° C.

4. 2-(2,2,2-Trichloroethoxycarbonyloxyimino)-2-phenylacetonitrile, mp 82° to 84° C.

EXAMPLE 3

[Preparation of carbonic acid esters]

A. Ether (10 ml.) was added to a solution of phosgene (2 g.) in benzene (12.4 ml.). A solution of 4-methoxybenzyl alcohol (2.76 g.) in ether (10 ml.) was added dropwise to the above solution for 25 minutes at −10° C with stirring. Careful attention should be directed to the heat given off in the above reaction. The mixture was stirred for 20 minutes at between −10° to −7° C and phosgene was removed by introducing a nitrogen stream for 15 minutes at the same temperature. A solution of diethyl 2-hydroxyiminomalonate (3.78 g.) in benzene (20 ml.) was added to the resultant solution containing 4-methoxybenzyl chloroformate, for 10 minutes and a solution of triethylamine (5.6 ml.) in benzene (20 ml.) was added for 30 minutes at between −7° C to −2° C. Benzene (20 ml.) was added thereto and the mixture was stirred for 30 minutes at 5° C. for 1 hour at room temperature and allowed to stand for 64 hours. Water was added to the reaction mixture to dissolve an insoluble material and the organic layer was then washed with water, 3 times with a 0.5M citric acid aqueous solution (20 ml.), 3 times with a 5% sodium carbonate aqueous solution (20 ml.) and a sodium chloride aqueous solution, and then dried over magnesium sulfate. After drying, the solvent was distilled off to give diethyl 2-(4-methoxybenzyloxycarbonyloxyimino)malonate (5.62 g.), oil.

B. A solution of ethyl chloroformate (2.17 g.) in benzene (10 ml.) was added dropwise to a solution of 1-hydroxy-6-chloro-1H-benzotriazole (3.38 g.) and triethylamine (2.80 ml.) in benzene (30 ml.) under ice-cooling and stirring. Benzene (30 ml.) was further added to the mixture and the reaction temperature was slowly elevated to room temperature the mixture was allowed to stand overnight. Precipitated crystals were filtered off and the filtrate was concentrated. Benzene was added to the residue and an insoluble material was filtered off. The filtrate was concentrated to give 1-ethoxycarbonyloxy-6-chloro1H-benzotriazole (2.2 g.), crystals. The precipitated crystals filtered off and the insoluble material in benzene were mixed and then washed with water, a sodium bicarbonate aqueous solution, 1N hydrochloric acid and water, and recrystallized from methanol (75 ml.) to give the desired compound (3.5 g.), white needles, mp 160° to 162° C.

Analysis: $C_9H_8N_3O_3Cl$: Calcd.: C, 44.73, H, 3.36, N, 17.39, Cl 14.67; Found: C, 44.71, H, 3.25 N, 17.34, Cl 14.72.

C. Benzyl chloroformate (8.5 g.) was added dropwise under ice-cooling to a solution of 1-hydroxy-1H-benzotriazole (6.8 g.) and triethylamine (7.0 ml.) in a mixture of benzene (100 ml.) and water (50 ml.), and the mixture was stirred for 3 hours at the same temperature. The reaction mixture was filtered and the precipitated crystals were washed with water and dried. The benzene layer was washed with water, dried and concentrated. The residue and the crystals obtained above were mixed and recrystallized from a mixed solvent of benzene and petroleum ether to give 1-benzyloxycarbonyloxy-1H-benzotriazole (12.1 g.), mp 130° to 131° C.

Analysis: $C_{14}H_{11}N_3O_3$: Calcd.: C, 62.44, H, 4.12, N, 15.61; Found: C, 62.62, H, 4.16, N, 15.49.

D. A solution of benzyl chloroformate (5.1 g.) in ether (40 ml.) was added to a solution of 2-hydroxyimino-2-phenylacetonitrile (4.4 g.) in a mixture of a 1N potassium hydroxide aqueous solution (30 ml.) and dioxane (10 ml.) under ice-cooling. The mixture was stirred for 1 hour at the same temperature and for 4 hours at room temperature. The ether layer was separated from the reaction mixture and the aqueous layer was further extracted with ether. Both ether layers were combined, washed with water and dried over magnesium sulfate. The solvent was distilled off and n-hexane was added to the residue. The precipitated crystals were collected by filtration to give 2-benzyloxycarbonyloxyimino2-phenylacetonitrile (5.2 g.), mp 73° to 75° C.

Infrared Absorption Spectrum (Nujol): 1795 cm$^{-1}$.

E. A solution of 2,2,2-trichloroethyl chloroformate (2.2 g.) in benzene (10 ml.) was added dropwise to a solution of 2-hydroxyimino-2-phenylacetonitrile (1.5 g.) and triethylamine (1.40 ml.) in benzene (20 ml.) at room temperature, the mixture was stirred for 3 hours at the same temperature. Benzene and water were added to the reaction mixture layer was washed with water and dried over magnesium sulfate. The solvent was distilled off and the residue was crystallized by adding a small of ether and n-hexane. The crystals were collected by filtration and recrystallized from methanol to give 2-(2,2,2-trichloroethoxycarbonyloxyimino)-2-phenylacetonitrile (2.7 g.), mp 82° to 84° C.

Infrared Absorption Spectrum (Nujol): 1800, 1790 cm$^{-1}$.

Analysis: $C_{11}H_7O_3N_2Cl_3$: Calcd.: C, 41.08, H, 2.19, N, 8.71, Cl, 33.08; Found: C, 41.29, H, 2.05, N, 8.81, Cl, 32.31.

F. The following compounds were obtained according to a method similar to those shown in Examples 3(A) to 3(E).

1. Ethyl 2-tert-butoxycarbonyloxyimininoacetoacetae, oil.

Infrared Absorption Spectrum (Film): 1780, 1730, 1690 cm$^{-1}$.

2. 2-tert-Butoxycarbonyloxyimino-1-phenylbutane-1,3-dione, mp 90° to 103° C (dec.).

3. 1-tert-Butoxycarbonyloxy-6-chloro-1H-benzotriazole, mp 98° to 100° C (dec.).

4. 2-tert-Butoxycarbonyloxyimino-2-phenylacetonitrile, mp 84° to 86° C.

5. 2-(4-Methoxybenzyloxycarbonyloxyimino)-2-phenylacetonitrile, mp 112° to 113° C.

6. Benzophenone O-tert-butoxycarbonyloxime, mp 131° to 133° C.

7. 2-tert-Butoxycarbonyloxyimino-2-(4-chlorophenyl)acetonitrile, mp 91 to 92° C.

8. 2-tert-Butoxycarbonyloxyimino-2-(1-naphthyl)acetonitrile, mp 90° to 92° C.

9. 2-(1-Cyclopropylethoxycarbonyloxyimino)-2-phenylacetonitrile, mp 65° to 67° C.

What we claim is:

1. Carbonic acid esters of the formula:

R'$_1$OCOOR'$_2$ ps wherein R'$_1$ is lower alkyl which may have substituents selected from the group consisting of halogen, lower alkoxy and aryloxy, or ar(lower) alkyl which may have substituents selected from the group consisting of lower alkoxy, halogen, nitro and cyano, and R'$_2$ is a group represented by the formula:

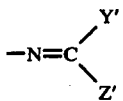

wherein Y' is selected from the group consisting of cyano, nitro, carbamoyl, esterified carboxy, lower alkanoyl, aroyl, di-substituted carbamoyl, or aryl which may have substituents selected from the group consisting of halogen, lower alkoxy, nitro, cyano and halo(lower)alkyl and Z' is aryl which may have substituents selected from the group consisting of halogen, lower alkoxy, nitro, cyano and halo(lower)alkyl; provided that when R'$_1$ is lower alkyl, Y' is cyano, and Z' is aryl, the number of carbon atoms of lower alkyl for $R'_1$ is 4 or 5.

2. The compounds according claim 1 wherein Y' is cyano, nitro, carbamoyl, esterified carboxy, lower alkanoyl, aroyl, di-substituted carbamoyl, or aryl which may have substituents selected from the group consisting of lower alkoxy, nitro, cyano, and halo(lower)alkyl and Z' is aryl which may have substituents selected from the group consisting of lower alkoxy, nitro, cyano and halo(lower) alkyl.

3. The compounds according to claim 2, wherein $R'_1$ is lower alkyl which may have halogen, or ar(lower)alkyl which may have lower alkoxy, Y' is aryl or cyano and Z' is aryl;

provided that when $R'_1$ is lower alkyl, Y' is cyano and Z' is aryl, the number of carbon atoms of lower alkyl for $R'_1$ is 4 or 5.

4. The compounds according to claim 3, wherein $R'_1$ is lower alkyl which may have halogen.

5. The compounds according to claim 4, wherein $R'_1$ is lower alkyl.

6. The compounds according to claim 5, wherein $R'_1$ is lower alkyl having 4 or 5 carbon atoms, Y' is cyano and Z' is aryl.

7. The compounds according to claim 6, wherein $R'_1$ is tert-butyl or 1-cyclopropylethyl and Z' is phenyl; or naphthyl.

8. The compounds according to claim 7, wherein $R'_1$ is tert-butyl.

9. The compound according to claim 8, wherein Z' is phenyl.

10. The compound according to claim 8, wherein Z' is naphthyl.

11. The compound according to claim 7, wherein $R'_1$ is 1-cyclopropylethyl and Z' is phenyl.

12. The compounds according to claim 5, wherein Y' is aryl and Z' is aryl.

13. The compound according to claim 12, wherein $R'_1$ is tert-butyl, Y' is phenyl and Z' is phenyl.

14. The compounds according to claim 4, where $R'_1$ is lower alkyl having halogen, Y' is cyano and Z' is aryl.

15. The compounds according to claim 14, wherein $R'_1$ is ethyl having chlorine and Z' is phenyl.

16. The compound according to claim 15, wherein $R'_1$ is 2,2,2-trichloroethyl.

17. The compounds according to claim 3, wherein $R'_1$ is ar(lower)alkyl which may have lower alkoxy, Y' is cyano and Z' is aryl.

18. The compounds according to claim 17, wherein $R'_1$ is benzyl which may have methoxy and Z' is phenyl.

19. The compounds according to claim 18, wherein $R'_1$ is benzyl or 4-methoxybenzyl.

20. The compound according to claim 19, wherein $R'_1$ is benzyl.

21. The compound according to claim 19, wherein $R'_1$ is 4-methoxybenzyl.

22. The compounds according to claim 1, wherein $R'_1$ is lower alkyl, Y' is cyano and Z' is aryl having halogen.

23. The compounds according to claim 22, wherein $R'_1$ is tert-butyl and Z' is phenyl having chlorine.

24. The compound according to claim 23, wherein Z' is 4-chlorophenyl.

* * * * *

UNITED STATES PATENT OFFICE
CERTIFICATE OF CORRECTION

PATENT NO. : 4,014,915
DATED : March 29, 1977
INVENTOR(S) : Masumi Itoh, et al

It is certified that error appears in the above-identified patent and that said Letters Patent are hereby corrected as shown below:

On the title page of the patent change the listing of the inventors to read as follows:

--Inventors: Masumi Itoh, Takatsuki, Japan; Takashi Kamiya, Suita, Japan and Daijiro Hagiwara, Ikeda, Japan Signed and Sealed this thirtieth Day of August 1977

[SEAL]

Attest:

RUTH C. MASON
*Attesting Officer*

C. MARSHALL DANN
*Commissioner of Patents and Trademarks*